United States Patent [19]
Röntgen-Odenthal et al.

[11] Patent Number: 4,828,844
[45] Date of Patent: May 9, 1989

[54] PULMONARY SURFACTANT

[76] Inventors: Renate Röntgen-Odenthal, Wasserackerstr. 16, 7800 Freiburg-Littenweiler; Manfred Dürr, Am blouen Stein 1o, 5024 Pulheim-Dansweiler; Ekkehard Harhausen, Käulchensweg 32, 5000 Köln 91, all of Fed. Rep. of Germany

[21] Appl. No.: 520,236

[22] Filed: Aug. 4, 1983

[30] Foreign Application Priority Data

Aug. 5, 1982 [DE] Fed. Rep. of Germany ........ 3229179

[51] Int. Cl.$^4$ .............................................. A61K 9/14
[52] U.S. Cl. ..................................... 424/489; 514/148
[58] Field of Search ........................... 424/176, 199, 38

[56] References Cited

U.S. PATENT DOCUMENTS

| | | | |
|---|---|---|---|
| 2,414,918 | 1/1947 | Abramson | 424/176 |
| 3,197,368 | 7/1965 | Lappe | 424/199 |
| 3,594,476 | 7/1971 | Merrill | 424/43 |
| 4,252,796 | 2/1981 | Yu et al. | 424/176 |

OTHER PUBLICATIONS

CA 99:65086w.
Freese et al. "Effects of Betamethasone and Fetal Sex on the Synthesis and maturation of Lung Surfactant Phosphalipids in Rabbits", Biochim. Biophys. Acta 750(1) 47–59, 1983.
Engle et al., "Type II Alicolar Cells in OrganoTypic Culture A Model System for the Study of Surfactant Synthesis, Biochem, BiophyseActa" 617(2) 225–236 (1980).
Rabinowitz et al. "Reutilization of Fatty Acid Carbons for Lung Lipid Synthesis", Am. J. Physiol. 1981, 240(4) E435–E440 (CA94:171661m).

Primary Examiner—Nicky Chan
Attorney, Agent, or Firm—Keil & Weinkauf

[57] ABSTRACT

A pulmonary surfactant for the treatment of dyspnea syndromes, containing dipalmitoyl phosphatidyl choline (DPPC) and dipalmitoyl phosphatidyl glycerol (DPPG) in a ratio of from 9:1 to 8:2 and a sugar, in the form of a redispersable powder, which is obtained by dissolving the phospholipids in glacial acetic acid, adding the sugar, and finally freeze-drying of the mixture. The lyophilisate is redispersed in a suitable buffer solution for application.

2 Claims, No Drawings

PULMONARY SURFACTANT

The object of the invention is a new pulmonary surfactant consisting of a mixture of dipalmitoyl phosphatidylcholine, dipalmitoyl phosphatidyl glycerol and a sugar in the form of a lyophilisate, and utilization of the surfactant after redispersion in a buffer solution, for the treatment of dyspnea syndromes.

More newborns die yearly of dyspnea syndomes than of any other disease. The cause is an excessive surface tension in the alveoli, which prevents the lungs from independently breathing. This in turn is caused by a deficiency in surfactant factors. This substance normally forms shortly before birth. The surface active substances needed for breathing are phospholipids which are formed in the alveolar cells of type II in the process of phospholipid metabolism. There will be an inadequate quantity of the substances if the child is born prematurely or is a Ceasarian delivery, is born before labor pains have begun, or if the mother is a diabetic.

In central Europe the rate of dyspnea syndrome in newborns is between 15 and 20%. To prevent and treat the syndrome, attempts have been made to stimulate phospholipid synthesis with glycocorticoides and bromohexine metabolites. The therapy with glycocorticoids involves a high risk and is therefore applied with much hesitation. Therapy with bromohexine metabolites has been abandoned for various reasons.

There have been no shortage of attempts, therefore, to discover as natural as possible a surfactant system to restore the needed surface tension in the pulmonary system.

U.S. Pat. No. 3,594,476 describes a pulmonary surfactant in aerosol form, in which dipalmitoyl phosphatidyl choline is dispersed in an aqueous sodium chloride solution. The resulting dispersions are not, however, sufficiently stable and have an inadequate degree of surface activity, so that they have not been adopted for therapeutic application.

DE-OS No. 30 21 006 describes pulmonary surfactant systems obtained from the lung tissue of mammals and consisting of phospholipids, cholesterol, carbohydrates, and protein. A disadvantage of these preparations is that they cannot be obtained in an unchanging composition and in the presence of foreign protein can promote the formation of antibodies against the surfactant protein.

Liposome suspensions of dipalmitoyl phosphatidyl choline and dipalmitoyl phosphatidyl glycerol in a ratio of 9:1 have proven to be usable (M. Obladen et al., Eur. J. Pediat. Vol. 1311, No. 4, 219–228 (1979)). These liposomes were produced by suspending or dispersing mixtures of dipalmitoyl phosphatidyl choline and dipalmitoyl phosphatidyl glycerol in an aqueous solution. The suspensions so created do not, however, display an adequate degree of stability and have a non-uniform surface activity.

The objective of the present invention is to create a pulmonary surfactant system that consists of dipalmitoyl phosphatidyl choline and dipalmitoyl phosphatidyl glycerol and which possesses a constant surface activity and remains stable over longer periods of storage.

Surprisingly, it was found that usable, stable pulmonary surfactant systems with a constant surface activity can be produced by dissolving dipalmitoyl phosphatidyl choline (DPPC) with dipalmitoyl phosphatidyl glycerol (DPPG), with a ratio of from 9:1 to 8:2, in glacial acetic acid, diluting the resulting solution with sugar, and then freeze-drying it.

The pulmonary surfactant obtained in this fashion, as a mixture of dipalmitoyl phosphatidyl choline and dipalmitoyl phosphatidyl glycerol and the usual adjuvants, is characterized by its being a redispersable powder with a content of 40–45 wght. % dipalmitoyl phosphatidyl choline,
5–10 wght. % dipalmitoyl phosphatiyl glycerol, and
50 wght. % sugar.

Preferred forms of the invention and the application of the pulmonary surfactant are described in the secondary claims.

8–9 parts by weight dipalmitoyl phosphatidyl choline and 2–1 parts by weight dipalmitoyl phosphatidyl glycerol (DPPG) each are dissolved in 10–30 parts by weight glacial acetic acid at about 20° to 40° C.; the separate solutions are combined during stirring, and sugar is added, namely 1 part sugar to 1 part DPPC/DPPG mixture.

Suitable sugars for use are glucose, fructose, or lactose. The solution obtained is sterilely filtered, if necessary, and, then freeze-dried according to the conventional methods. The resulting lyophilisates have an excellent stability, even after a longer period of storage (1 year). The lyophilsate is redispersed before being used in a buffer solution. The homogeneous dispersion obtained can be administered in intrapulmonary or intratracheal fashion. Suitable buffer solutions are those commonly used by the specialist, particularly phosphate buffers.

EXAMPLE 1

45 mg dipalmitoyl phosphatidyl choline and 5 dipalmitoyl phosphatidyl glycerol are each dissolved in 1 ml glacial acetic acid (98%) while being heated. The clear, warm solutions are combined while being stirrred and 50 mg glucose is added. The solution is poured into a 10 ml glass container and lyophilized, and the glass container is sealed.

Before application the lyophilisate is redispersed in 1.00 ml tris-buffer 0.35% (tris-buffer 0.6%, $H_2O$, phosphate buffer).

Measurement of Surface Activity

The measurements were made with a modified Wilhelmy scale

The active material was added in dispersion form to the surface of a physiological saline solution, in a quantity of 2.55 $\mu$/cm$^2$ at a temperature of 3720 C.

In judging the surface activity both the stability index (SI) and the hysteresis curve were employed.

A maximum surface tension range of 61–68 dyn/cm was ascertained and a minimum surface tension range of 0–1 dyn/cm in 50–75% of the compressable surface area. The stability index was 1.95–2.00.

EXAMPLE 2

A mixture of 45 mg dipalmitoyl phosphatidyl choline and 10 mg dipalmitoyl phosphatidyl glycerol were combined in the same fashion as Example 1.

EXAMPLE 3

50 mg lactose were used instead of glucose in the process described in Example 1.

EXAMPLE 4

50 mg lactose were used instead of glucose in the process described in Example 2.

We claim:

1. A stable and dispersible pulmonary surfactant powder which comprises: from about 40 to 45 percent by weight of dipalmitoyl phosphatidyl choline, from about 5–10 percent by weight of dipalmitoyl phosphatidyl glycerol, and about 50 percent by weight of a sugar selected from the group consisting of glucose, fructose and lactose.

2. A method for treating human respiratory distress syndrome which comprises first forming a homogeneous dispersion from a pulmonary surfactant powder comprised of from about 40 to 45 percent by weight of dipalmitoyl phosphatidyl choline, from about 5–10 percent by weight of dipalmitoyl phosphatidyl glycerol, and about 50 percent by weight of a sugar selected from the group consisting of glucose, fructose and lactose; and thereafter passing the dispersion into the trachea and lungs.

* * * * *